United States Patent [19]

Aslam et al.

[11] Patent Number: 5,132,437
[45] Date of Patent: Jul. 21, 1992

[54] SYNTHESIS OF 1-AMINOANTHRAQUINONE

[75] Inventors: Mohammad Aslam; Daniel A. Aguilar, both of Corpus Christi, Tex.

[73] Assignee: Hoechst Celanese Corporation, Somerville, N.J.

[21] Appl. No.: 654,842

[22] Filed: Feb. 12, 1991

[51] Int. Cl.$^5$ .................... C07C 279/34; C07C 2/68
[52] U.S. Cl. .................... 552/238; 585/466; 585/468; 585/469; 552/251; 568/34; 568/58; 568/67; 568/640; 568/744; 568/928
[58] Field of Search ............ 552/238, 251; 585/469, 585/466, 468; 568/34, 58, 67, 640, 744, 928

[56] References Cited

U.S. PATENT DOCUMENTS

| | | | |
|---|---|---|---|
| 3,873,538 | 3/1975 | Oxford et al. | 260/247.2 R |
| 3,959,318 | 5/1976 | Torisu et al. | 260/369 |
| 3,966,774 | 6/1976 | Stoll et al. | 260/378 |
| 4,105,680 | 8/1978 | Chung | 260/378 |
| 4,328,161 | 5/1982 | Chung | 260/378 |
| 4,379,092 | 4/1983 | Devic | 260/369 |
| 4,804,501 | 2/1989 | James et al. | 260/369 |
| 4,874,483 | 3/1989 | Blank et al. | 585/462 |

*Primary Examiner*—C. Warren Ivy
*Assistant Examiner*—Raymond Covington
*Attorney, Agent, or Firm*—S. D. Frenkel; D. R. Cassady

[57] ABSTRACT

1-Aminoanthraquinone (1-AAQ) is synthesized by the reaction of 2-chlorobenzyl chloride and xylene in the presence of a solid acid catalyst to yield 2-chloro dimethyldiphenylmethane, subsequent oxidation of the methyl groups, ring closure to form a 1-chloroanthraquinone carboxylic acid, replacement of the 1-chloro group with ammonia, and decarboxylation.

30 Claims, No Drawings

SYNTHESIS OF 1-AMINOANTHRAQUINONE

BACKGROUND OF THE INVENTION

The present invention relates to a novel synthetic route for the production of 1-aminoanthraquinones.

1-Aminoanthraquinone is a well known and important intermediate used in the preparation of colorants including dyes and pigments as well as other specialty chemicals. 1-Aminoanthraquinone is particularly useful as an intermediate in the preparation of fiber-reactive dyes. Thus, in the past, most dyes were dispersed dyes which relied on surface properties such as static interaction to bond to a fabric. Presently, new fiber-reactive dyes which react with chemical sites on the fabric fibers have provided a significant improvement in the ability of the dye to remain bonded to the fabric. 1-Aminoanthraquinone is an intermediate for the formation of such fiber-reactive dyes. For example, 1-amino-4-bromoanthraquinone-2-sulfonic acid (Bromamine Acid), an important intermediate in a fiber reactive dye, can be formed by treatment of 1-aminoanthraquinone with oleum or chlorosulfonic acid to form the 1-aminoanthraquinone-2-sulfonic acid derivative which is then followed by treatment with bromine. This brominated compound can be subsequently reacted with another compound which can couple with the fabric fiber. Importantly, the chromophore, i.e., the 1-aminoanthraquinone, becomes part of the molecule which couples with the fabric fiber. It is important that the amino group be located on the 1 position of the anthraquinone inasmuch as the placement of the amino group on other positions of the anthraquinone yields a color body of a different color.

1-Aminoanthraquinone has been prepared by the reaction of anthraquinone with oleum in the presence of mercury to produce anthraquinone-1-sulfonic acid which, in turn, is reacted with ammonia. However, mercury is a known toxic chemical and thus, poses severe environmental problems with its use. In an alternative process to produce 1-aminoanthraquinone, anthraquinone is nitrated directly followed by reduction of the nitroanthraquinone. Unfortunately, direct nitration of anthraquinone yields a mixture of products including 1-, 2-, and dinitroanthraquinones which upon hydrogenation yield the corresponding aminoanthraquinone mixture. Consequently, the product which is formed subsequent to reduction yields more than one color body and intricate methods of separation must be used to obtain the pure 1-aminoanthraquinone. Not only with nitration, but with other processes which attempt to add a functional group which can be converted to an amino group, selectivity to the 1-position is marginal as other isomers are formed or complicated process schemes are required to fix the amino group at the 1-position on the anthraquinone.

Accordingly, it is an object of the present invention to provide a commercially feasible and economical process for the selective production of 1-aminoanthraquinone and substituted derivatives thereof without the disadvantages of the prior art processes as mentioned above.

SUMMARY OF THE INVENTION

According to the invention, 1-aminoanthraquinone and substituted derivatives thereof are formed having the general formula:

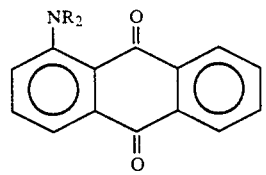

in which R represents hydrogen, alkyl, cycloalkyl, or aryl. The anthraquinone may be substituted as long as the substituents do not adversely affect the process for producing the 1-aminoanthraquinone as described below.

The invention involves a novel process scheme to form 1-aminoanthraquinone, which scheme includes a series of novel reactions and the formation of a novel intermediate compound mixture. Briefly, as depicted below 1-aminoanthraquinone and 1-aminoanthraquinone-carboxylic acid are prepared by a synthesis which involves the steps of (i) solid acid-catalyzed reaction of 2-substituted benzyl compound, (1) with xylene (2) to afford 2-substituted dimethyldiphenylmethane (3); (ii) air oxidation to afford 2-substituted benzophenonedicarboxylic acid (4); (iii) oleum-catalyzed ring closure to afford a mixture of 1-substituted anthraquinonecarboxylic acid isomers (5); (iv) ammonolysis to afford 1-aminoanthraquinonecarboxylic acid (6); and (v) decarboxylation to afford 1-aminoanthraquinone (7).

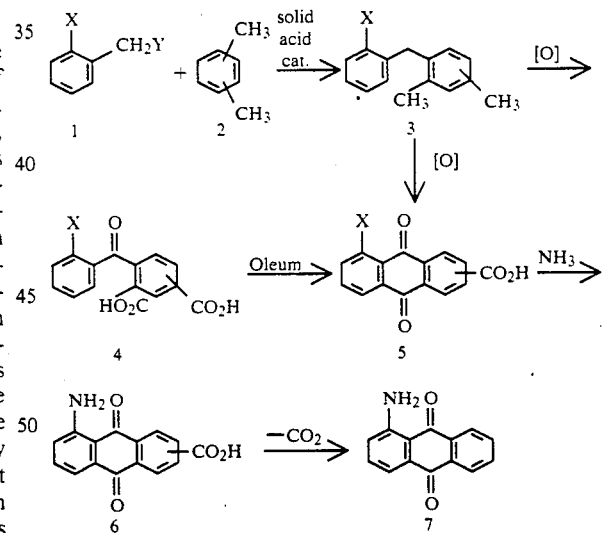

wherein X and Y may be the same or different, and wherein X and Y are selected from the group consisting of halogen, hydroxy, nitro, thioalkyl, alkoxy, or a sulfonyl-containing group.

The process scheme of this invention utilizes inexpensive starting materials, avoids toxic catalysts such as mercury used in the prior art and fixes the leaving group for substitution with amino at the beginning of the process to provide excellent selectivity to the 1-aminoathraquinone without the need for purification or cumbersome reaction mechanisms to provide the desired selectivity.

DETAILED DESCRIPTION OF THE INVENTION

In the first step (i) of the process to form 1-aminoanthraquinone as in the present invention, a 2-substituted benzyl compound depicted as compound 1 above is reacted with xylene in the liquid phase in the presence of a solid acid catalyst. The substituents X represent a leaving group and may be the same or different. Typical leaving groups include the halogens, hydroxy, alkoxy, nitro and sulfonyl including organosulfonyl groups such as tosylate, mesylate, etc. The preferred leaving group is a halogen with the most preferred being chlorine. The most preferred starting compound 1 is 2-chlorobenzyl chloride depicted as compound 8 herein:

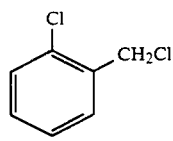

Since a leaving group is fixed at the 2-position of compound 1 used at the start of the process of this invention, 1-aminoanthraquinone can be selectively produced without the need for cumbersome separation of isomers. In the present invention, the 1-amino group is fixed by the use of the leaving group at the 2-position of compound 1 at the very start of the reaction scheme. The starting xylene designated as compound 2 above can be ortho-, meta- or para-xylene. Para-xylene is preferred.

The reaction of 2-substituted benzyl compound 1 with xylene takes place in the liquid phase in the presence of a solid acid catalyst. A solvent which is inert to the reactants may be utilized. Non-limiting examples of solvents include the halogenated solvents such as methylene chloride, chloroform, etc. Also, the reaction may be run using an excess of xylene which is useful as a solvent. An excess of 2-substituted benzyl compound 1 should be avoided inasmuch as once all of the xylene is reacted, the excess leaving groups on the excess benzyl compound may react with the product which is formed.

The solid acid catalysts may be chosen from among alumina, silica-alumina, aluminophosphates, aluminosilicates such as large and medium pore zeolites and less acidic homologues of the zeolites such as silicalites. The solid catalysts have several advantages over homogeneous catalysts such as improved thermal stability, selectivity as well as ease of separation and handling. Silica-alumina is the preferred catalyst.

The temperature of reaction can range from about 80°–160° C., preferably 100°–150° C. and most preferably about 140°–150° C. Pressure is not critical and additional pressure other than that formed by the vapor of the solvents is not needed, although, not believed to be undesirable. Upon completion of the reaction, excess xylene is distilled to leave a liquid product having a b.p. of 138°–140° C. at 0.05 mm Hg.

The product which is formed in step (i) comprises 2-substituted-2', (3', 4' or 5')-dimethyldiphenylmethane which is designated as compound 3 in the reaction scheme described previously. The placement of the methyl group at the 3', 4' or 5' position of the formed diphenylmethane will depend on whether ortho-, meta- or paraxylene was reacted, respectively.

In step (ii) of the process, the 2-substituted-dimethyldiphenylmethane is oxidized to yield a 2-substituted benzophenone dicarboxylic acid which is designated as compound 4 in the process scheme described above. Any oxidation process which can successfully oxidize the methyl groups to carboxyl groups can be used in this step of the process. Liquid phase chemical oxidation agents such as alkali metal dichromates, e.g., potassium dichromate, sodium dichromate and potassium permanganate, etc. can be used. However, oxidation with chemical agents is not preferred. For one, it has been found that oxidation using chemical oxidizing agents does not provide very high yields of the desired product and, subsequent to reaction there is a problem of disposing of the chemical agents. The preferred method is the liquid phase air oxidation of the 2-substituted dimethyl diphenylmethane.

The air oxidation of the 2-substituted-dimethyldiphenylmethane to the corresponding dicarboxylic acid is preferably accomplished in air under pressure in acetic acid in the presence of a cobalt-manganese-bromide catalyst as described in U.S. Pat. No. 4,804,501 which is hereby incorporated by reference herein. It has further been found that air oxidation of the 2-substituted-dimethyl benzophenone can result in the direct formation of anthraquinonecarboxylic acid depicted as compound 5 in the above reaction scheme. Analytical data has shown a small but significant amount of the air oxidation product to be anthraquinonecarboxylic acid. Obviously, air oxidation may provide a substantial savings if the oleum cyclization can be deleted from the reaction scheme.

The weight ratio of 2-substituted dimethyl diphenylmethane to acetic acid is in the range of from about 1:1 to about 1:20, preferably in the range of from about 1:4 to about 1:20. The cobalt-manganese-bromide catalyst which is used has a mole ratio of cobalt to manganese of about 1.0:0.1 to about 1.0:10.0, and mole ratio of bromide to total metals of the catalyst is from 0.2:1.0 to about 20.0:1.0. Preferably, the mole ratio of cobalt-to-manganese is from about 1.0:0.1 to about 1.0:10.0, and the mole ratio of bromide to total metals of the catalyst is from about 3.0:1.0 to about 10.0:1.0. The process comprises oxidation of the 2-substituted dimethyldiphenylmethane at a temperature within the range of from about 75° C. to about 250° C. at a pressure of from about 1 to about 100 atmospheres.

An alternative oxidation catalyst which can be used is a zirconium-cobalt-manganese-bromide catalyst wherein the mole ratio of zirconium to cobalt is about 0.005:1.0 to about 0.20:1.0; the mole ratio of cobalt to manganese is from about 1.0:0.1 to about 1.0:10.0, and mole ratio of bromide to total metals of catalyst is from about 0.2:1.0 to about 20.0:1.0. Preferably, the mole ratio of zirconium to cobalt in the catalyst is from about 0.01:1.0 to about 0.10:1.0 and the mole ratio of cobalt-to-manganese is from about 1.0:0.1 to about 1.0:10.0 and the mole ratio of bromide to total metals of the catalyst is from about 3.0:1.0 to about 10.0:1.0.

In step (iii) of the process to form 1-aminoanthraquinone according to the present invention, ring closure of the 2-substituted benzophenone dicarboxylic acid is achieved by acid catalysis. Preferably, the ring closure to form the 1-substituted anthraquinone carboxylic acid (5) is done by reacting the 2-substituted benzophenone dicarboxylic acid with about 10 to 40% oleum in concentrated sulfuric acid. The temperature of the reation can range from about room temperature to 120° C., preferably 60°–100° C. and most preferably from about 90°-95° C. The reaction should run from about 2 to about 6 hours.

It has been found, at least with respect to cyclization of the 2-substituted benzophenone 2',5'-dicarboxylic acid which results when utilizing para-xylene in step (i) of the process, that this compound undergoes Hayashi rearrangement to afford a mixture of two dicarboxylic acids, the 2-substituted benzophenone 2',4'-dicarboxylic acid and the 2-substituted benzophenone-2',5'-dicarboxylic acid. Upon cyclization, what is formed is a mixture of 1-substituted anthraquinone carboxylic acid isomers in which the carboxyl group is located at the 6- or 7-position on the anthraquinone. The mixture comprises approximately a 50:50 ratio of the individual isomers. It is believed that a similar isomerization will occur upon cyclization of the 2-substituted benzophenone dicarboxylic acids which have been formed from ortho- or meta-xylene at the beginning of the process scheme of this invention.

Although the use of oleum for ring closure is preferred, other known cyclization catalysts can be used. For example, sulfuric acid, phosphoric acid, HF or an HF/$BF_3$ catalyst at a temperature of about 50° C. to about 100° C. can also be utilized. Isomerization using this latter catalyst has also been found.

Step (iv) of the process of this invention is the ammonolysis of the 1-substituted anthraquinone carboxylic acid. The 1-substituted anthraquinone carboxylic acid is reacted with any amine of the formula $RNH_2$ wherein R can be hydrogen, alkyl, cycloalkyl and aryl. Since the anthraquinone which is formed during cyclization in Step (iii) of the present process contains a carboxylic acid moiety, the 1-substituted anthraquinone carboxylic acid is water soluble and the ammonolysis may take place in water. If desired, organic solvents may be included. However, the water solubility of the precursor formed in the present invention is a clear advantage over reaction mechanisms which require organic solvent systems for nitration. The reaction may take place in the presence of a copper catalyst, if desired. The use of the catalyst reduces the reaction time. However, less yield of the desired 1-aminoanthraquinone carboxylic acid results as other byproducts are formed. On the other hand, without the catalyst, the reaction times are relatively long but yields of the desired product are substantially higher than those achieved with the catalyst. Reaction temperatures are not overly critical with a typical temperature ranging from about 100°-150° C. Although not overly critical, it is important to note that a temperature which is too high may cause the desubstitution at the 1 position of the anthraquinone. Obviously, at too low a temperature, little or no reaction takes place.

The final step (v) of the process of this invention is the decarboxylation of the 1-aminoanthraquinone carboxylic acid. Decarboxylation is a known process and is typically achieved by heating the 1-aminoanthraquinone carboxylic acid in a solvent in the presence of a catalyst such as copper, iron, tin or zinc. Copper or copper oxide is the preferred catalyst in this invention. The solvents which can be used include n-methyl-pyrrolidone, pyridine, quinoline and acetic acid. Pyridine is preferred. The temperature of the reaction should be from about 200°-350° C. with a preferred range of about 230°-270° C.

The 1-aminoanthraquinones formed by the process of this invention can be used as intermediates for dyes for fabrics, dyes for hair, pigments, printing inks, electro-optical device colorants, photographic sensitizer, DNA binding, antitumor properties, and chromophoric compounds for determination of biological compounds.

The following examples illustrate the investigation of the individual reactions which form the process scheme of this invention. The examples are illustrative only and should not be construed as limiting the invention to the embodiments shown in such examples.

EXAMPLE 1

This and the following example illustrate step (i) of the process of this invention, in particular, the formation of 2-chloro-2',5'-dimethyldiphenylmethane.

Davison Silica-Alumina Catalyst 979 was obtained in the form of pellets. The pellets were crushed to a powder of 200+ mesh size and calcined for 3 hours at 450° C. in air. The powder was kept in a closed container to prevent contact with atmospheric moisture.

The reaction below was monitored by an Hewlitt-Packard 5890A Gas Chromatograph equipped with a DBI-30W capillary column (0.32 mm ID×50 m).

A 5-1, 3-neck flask was equipped with a mechanical stirrer, a reflux condenser, a pressure equalizing addition funnel, and a heating mantle. The reflux condenser was fitted with a nitrogen purge and a gas outlet to remove HCl vapors. The flask was charged with 2,000 ml of p-xylene and 100 g of calcined Davison Silica-Alumina Catalyst 979 powder. The mixture was stirred and heated at reflux, then a solution of 402.5 g (2.5 mol) of 2-chlorobenzylchloride in 500 ml of p-xylene was added over 2 hr. The mixture was allowed to reflux for one hour after the addition, then an aliquot was removed, filtered and analyzed by GC. The chromatogram indicated that reaction was essentially complete with less than 1.5% of 2-chlorobenzylchloride remaining. The reaction mixture was cooled to room temperature and the catalyst separated by filtration. Concentration in vacuo (at about 50 mm Hg) afforded 588.0 g of a brown liquid, which was distilled (b.p. 138-140 C./0.05 mm Hg) under reduced pressure to give 506.9 g of a clear, colorless liquid (Analysis: 97.2% one component by GLC).

EXAMPLE 1A

Three catalysts were selected for the experiments. One was Silicalite S-115, which is made by Union Carbide and is similar to Mobil's H-ZSM-5, and the others were Davison Silica-alumina 979 and gamma-alumina from BASF. The Davison catalyst was the most acidic catalyst. Silicalite S-115 is less acidic and usually exhibited lower conversions with higher selectivities.

In the runs, all catalysts were effective (see Table I). It was felt that the higher acidity of the Silica-Alumina would allow for lower catalyst charging. From Table I, it can be seen that in reacting m-xylene three monoalkylated isomers and at least two dialkylated isomers were produced. This is typical for Friedel-Crafts alkylations since the products are activated towards further alkylation. Distillation improved the purity of the monoalkylated isomer (as a mixture) to over 95%. Further purification of the major monoalkylated isomer from the other two was difficult. It was believed that the major monoalkylated isomer was the 2-chloro-2',4'-dimethyldiphenylmethane isomer, although this was not rigorously proven. All three isomers have very similar mass spectral fragmentation patterns.

TABLE I

Alkylation of Xylene with 2-Chlorobenzyl Chloride

| Exper. No. | xylene (ml) | mmol CBCl | catalyst (g) | Temp (°C.) | Time (hr) | conv. (%) | Selectivity I[a] | II[b] | III[c] | IV[d] |
|---|---|---|---|---|---|---|---|---|---|---|
| 1 | 50[e] | 0.05 | 979(5) | 140 | 1 | >99 | 71.1 | 15.9 | 3.9 | 4.2 |
| 2 | 50[e] | 0.05 | S-115(5) | 140 | 1 | >99 | 58.1 | 13.6 | 2.5 | 18.0 |
| 3 | 50[e] | 0.05 | Al$_2$O$_3$(5)[f] | 140 | 1 | 72 | 77.4 | 10.7 | 3.5 | 4.7 |
| 4 | 50[g] | 0.05 | 979(4) | 140 | 1 | >99 | 89.1 | 0.4 | 0.4 | 4.8 |
| 5 | 50[g] | 0.05 | γ-Al$_2$O$_3$ | 140 | 2 | >99 | 91.9 | 0.5 | 0.1 | 4.6 |

[a] major monoalkylated product
[b] minor monoalkylated product
[c] minor monoalkylated product
[d] dialkylated product mixture
[e] m-xylene as solvent
[f] BASF Alumina
[g] p-xylene as solvent

EXAMPLE 2

TABLE II

Synthesis of 1-Chloroanthraquinonecarboxylic Acids (1-CAQCA) from 2-Chlorobenzophenonedicarboxylic Acids (CBDA).

| Exper. No. | CBDA (g. mol) | 98% H$_2$SO$_4$ mL | 20% Oleum mL | Time (h) | Temp (°C.) | Yield[c] (g) | Yield[d] mol. | Conv. (%) | Yield (%) 1-CAQCA |
|---|---|---|---|---|---|---|---|---|---|
| 1[a] | 121.6, 0.4 | 400 | 200 | 4.5 | 90 | 108.0 | 0.38 | 100 | 94.0 |
| 2[b] | 243.3, 0.8 | 800 | 400 | 4.5 | 90 | 218.2 | 0.73 | 100 | 91.0 |
| 3[b] | 243.2, 0.8 | 800 | 400 | 4.5 | 90 | 217.0 | 0.74 | 100 | 92.0 |
| 4[b] | 121.8, 0.8 | 400 | 200 | 4.5 | 90 | 110.0 | 0.36 | 98 | 89.0 |
| 5[a] | 121.8, 0.8 | 400 | 200 | 4.5 | 90 | 107.0 | 0.36 | 100 | 91.0 |

[a] 2-Chlorobenzophenone-2',5'-dicarboxylic acid was used as starting material.
[b] 2-Chlorobenzophenone-2',4'-dicarboxylic acid is used as starting material.
[c] Yield of the crude product.
[d] Moles of pure products determined after HPLC-analysis.

This example illustrates the oxidation of 2-chloro-2',5'-dimethyldiphenylmethane to form both 2-chloro-2',5'-benzophenonedicarboxylic acid and 1-chloroanthraquinone-6/7-carboxylic acid.

A 1.0 Kg sample of 2-chloro-2',5'-dimethyldiphenylmethane was subjected to air-oxidation at a temperature of about 90° C. in a bubbler-type column to provide a two product mixture comprising about 78% by weight of 2-chloro-2',4'benzophenone dicarboxylic acid and about 15% by weight of 1-chloroanthraquinone-6/7-carboxylic acid.

EXAMPLE 3

This example illustrates the oleum-catalyzed ring closure of the 2-chloro-benzophenonedicarboxylic acid to 1-chloro anthraquinonedicarboxylic acid.

To a 3 liter, round bottomed flask equipped with a condenser, a thermometer and a stirrer, 2-Chloro-2',4' or (2',5')-benzophenonedicarboxylic acid, conc. sulfuric acid (98%) and 20% oleum were added. See Table II for a description of starting materials and proportions of reactants. The reaction mixture was heated to 90° C. and stirred for 4.5 hours in all cases. Ice/water (850 mL) was slowly added to the reaction mixture and the product precipitated as a light green solid. The solid was filtered, washed with 70% sulfuric acid (2100 mL) and water (20 l) until the washings were not very acidic (pH>2). The solid was dried in vacuum oven at 60-80 C. for 2 days to afford the product. See Table II for product yields.

The product formed in each case was a mixture of 1-chloroanthraquinone (-6- and -7-) carboxylic acid. Apparently the starting material undergoes Hayashi Rearrangement to afford a mixture of two dicarboxylic acids 2-chloro-benzophenone 2',(4' and 5')dicarboxylic acids. The two acids upon cyclization gave the corresponding anthraquinones.

Cyclization of 2-chlorobenzophenone 2',4'dicarboxylic acid (15.2 g) to 1-chloroanthraquinone carboxylic acids was also carried out in HF/BF$_3$ at 60° C. for 3 hours. After removal of HF/FB$_3$ by nitrogen purge and neutralization of the reaction mixture using aqueous KOH, a brown solid (4.0 g) was isolated. LC-analysis of the solid revealed it to contain the mixture as described above (48%), corresponding to a 13% yield. C-NMR spectrum of the solid revealed the two isomers were present in approximately 2:1 ratio.

EXAMPLE 4

Ammonolysis of 1-chloroanthraquinonecarboxylic Acid (1-CAQCA) was investigated using aqueous ammonia for the synthesis of 1-aminoanthraquinone-6- and -7-carboxylic acids (1-AAQCA). The results and process conditions are summarized in Table III. It was found that in the absence of a copper catalyst, 1-chloroanthraquinone carboxylic acid could be converted to 1-aminoanthraquinone carboxylic acid without significant formation of anthraquinone-2-carboxylic acid (AQCA).

The reaction of 1-CAQCA with aqueous ammonia in the presence of 1 mol equivalent of NaOH at 138°–142° C. for ~30 hours (Exper. No. 6) affords 1-AAQCA. The reaction proceeded with 98% conversion. 1-AAQCA was isolated in 76% yield (based on the combined response factors for 1-AAQ-6-CA and 1-AAQ-7-CA). The product also contained anthraquinone-2-carboxylic acid (AQCA) (4.1%) and a purple compound (5%). The purple compound and the two isomers (1-AAQ-6-CA and 1-AAQ-7-CA) were separated via preparative HPLC. The purple compound was characterized as diaminoanthraquinonecarboxylic acid (DAAQCA).

The 1-CAQCA was also reacted with concentrated (28-30%) aqueous ammonia in the presence of potassium carbonate and air (100 psig) for 30 hours. After acidification of the aqueous reaction mixture with dilute acid, for example HCl or $H_2SO_4$, to a pH of about 1-4, a reddish brown solid is precipitated. The solid is isolated by filtration, washed with water, and dried in a vacuum oven at about 70° C. and 50 mm Hg (Exper. No. 7). The reaction proceeded with 95% conversion. 1-AAQCA was isolated in 90% yield. Small amounts of AQCA (1.1%) and DAAQCA (6%) were also formed in this reaction.

Ammonolysis with anhydrous ammonia in 1,2-dimethoxyethane at 140° C. for 3.5 hours proceeded with 49% conversion and low (~8%) 1-AAQCA yield (Exper. No. 11). Ammonolysis of 1-CAQCA in DMF at 140° C. for 5 hours proceeded with 97% conversion but low (3%) 1-AAQCA yield (Exper. No. 17). A significant amount (30%) of DAAQCA was the major impurity in this reaction. Reaction with ammonia in methanol at 140° C. was attempted. Analysis of a sample obtained after 5 hours suggested a very slow reaction and significant accumulation of unwanted products. At this point the reaction was terminated.

Ammonolysis of 1-CAQCA with anhydrous ammonia at 65° C. for 4 hours was unsuccessful and unreacted 1-CAQCA was recovered. Reaction of 1-CAQCA with anhydrous ammonia at a high pressure (1000 psig starting pressure, with $N_2$) at 120° C. for 3 hours gave a very low yield (Exper. No. 12). Ammonolysis with anhydrous ammonia in o-dichlorobenzene at 125° C. for 3.5 hours was unsuccessful (Exper. No. 9). Again, unreacted starting material was recovered.

It was observed that the rate of ammonolysis increased significantly with the use of copper catalysts. Ammonolysis of 1-CAQCA with Cu(O), Cu(I) and Cu(II) in ~20% aqueous ammonia afforded 1-AAQCA in 66-73% isolated yield. The actual yield in these reactions may be 10-15% higher than the isolated yield, due to the loss of material removed as samples during the reaction. These reactions proceeded with 97-99% conversion in 4-6 hours. AQCA was the main impurity (4-6%).

TABLE III

Synthesis of 1-Aminoanthraquinonecarboxylic Acids (1-AAQCA) from 1-Chloroanthraquinonecarboxylic Acids (1-CAQCA).

| Exper. No. | 1-CAQCA (g, mmol) | Base (g) | Catalyst (g) | $N_2$/Air psig | Solvent (ml) | Aq. $NH_3$ 28% (mL) | Temp (°C.) | Time (h) | Total wt. (g) |
|---|---|---|---|---|---|---|---|---|---|
| 1 | 15, 52 | — | — | $N_2$, 50 | — | 150 | 140 | 26 | 13.9 |
| 2 | 15, 52 | — | — | Air, 50 | — | 150 | 140 | 24 | 13.6 |
| 3 | 15, 52 | — | — | Air, 50 | $H_2O$, 75 | 75 | 140 | 48 | 13.3 |
| 4 | 30, 105 | — | — | $N_2$, 50 | — | 300 | 140 | 44 | 26.3 |
| 5 | 45, 157 | — | — | $N_2$, 50 | — | 400 | 140 | 38 | 39.3 |
| 6 | 80, 280 | NaOH, 11.2 | — | $N_2$, 50 | — | 800 | 140 | 30 | 70.5 |
| 7 | 140, 469 | $K_2CO_3$, 61 | — | Air, 100 | — | | 140 | 30 | 124.1 |
| 8 | 10, 34 | — | — | Air, 100 | — | $100^b$ | 140 | 11 | 6.0 |
| 9 | 10, 34 | — | — | Air, 100 | $DCB^d$, 100 | $30^e$ | 125 | 3.5 | 13.2 |
| 10 | 5, 17 | — | $AgNO_3$ 0.15 | $N_2$, 85 | — | 100 | 140 | 5 | 4.2 |
| 11 | 10, 34 | — | — | $N_2$, 65 | DME, 100 | $30^e$ | 140 | 3.5 | 8.9 |
| 12 | 5, 17 | — | — | $N_2$, 1000 | — | $75^e$ | 120 | 1.5 | 3.6 |
| 13 | 5, 17 | — | — | $N_2$, 1000 | — | 75 | 140 | 4 | 4.0 |
| 14 | 5, 17 | $NaHCO_3$, 2.0 | MgO/CuO 0.04/0.07 | $N_2$, 80 | $H_2O$, 25 | 50 | 140 | 4 | 4.0 |
| 15 | 5, 17 | $NaHCO_3$, 2.0 | MgO, 0.04 | $N_2$, 80 | $H_2O$, 25 | 50 | 140 | 5 | 4.3 |
| 16 | 5, 17 | $NaHCO_3$, 2.0 | $CuCl_2$, 0.15 | $N_2$, 80 | $H_2O$, 25 | 50 | 140 | 4 | 4.4 |
| 17 | 5, 17 | $NaHCO_3$, 7.7 | — | Air, 100 | DMF, 100 | $20^e$ | 140 | 5 | 2.0 |
| 18 | 5, 17 | $NaHCO_3$, 7.7 | $CuWO_4$, 0.28 | $N_2$, 80 | $H_2O$, 25 | 50 | 140 | 4.5 | 4.0 |
| 19 | 5, 17 | $NaHCO_3$, 7.7 | CuCl, 0.09 | $N_2$, 80 | $H_2O$, 25 | 50 | 140 | 4.5 | 4.4 |
| 20 | 5, 17 | $NaHCO_3$, 7.7 | NiOAc, 0.3 | $N_2$, 80 | $H_2O$, 25 | 50 | 140 | 4.5 | 4.2 |
| 21 | 5, 17 | $NaHCO_3$, 7.7 | Cu, 0.06 | $N_2$, 80 | $H_2O$, 25 | 50 | 140 | 4 | 4.0 |
| 22 | 5, 17 | $NaHCO_3$, 7.7 | Cu, 0.06 | $N_2$, 80 | $H_2O$, 25 | 50 | 140 | 4.5 | 4.3 |
| 23 | 5, 17 | $Na_2CO_3$, 3.7 | $CuCl_2$, 0.15 | $N_2$, 80 | $H_2O$, 25 | $50^f$ | 140 | 4.5 | 4.0 |
| 24 | 5, 17 | $NaHCO_3$, 7.7 | $CuCl_2$, 0.15 | $N_2$, 80 | $H_2O$, 25 | $50^g$ | 140 | 5 | 4.0 |
| 25 | 5, 17 | $NaHCO_3$, 7.7 | $CuOAc_2/MnAc_2$ 0.18/0.26 | $N_2$, 80 | $H_2O$, 25 | 50 | 140 | 4 | 4.0 |
| 26 | 5, 17 | $NaHCO_3$, 7.7 | $CuCl_2$, 0.15 | $N_2$, 80 | $H_2O$, 25 | 50 | 130 | 6 | 4.1 |
| 27 | 5, 17 | $NaHCO_3$, 7.7 | $CuCl_2$, 0.075 | $N_2$, 80 | $H_2O$, 25 | 50 | 140 | 4 | 4.0 |
| 28 | 5, 17 | $NaHCO_3$, 7.7 | $CuCl_2$, 0.075 | $N_2$, 80 | $H_2O$, 25 | 50 | 140 | 4 | 4.5 |
| 29 | 5, 17 | $NaHCO_3$, 7.7 | $CuCl_2$, 0.03 | $N_2$, 80 | $H_2O$, 25 | 50 | 140 | 5 | 4.0 |
| 30 | 5, 17 | $NaHCO_3$, 7.7 | $CuCl_2$, 0.075 | $N_2$, 80 | — | $75^b$ | 140 | 4 | 4.2 |
| 31 | 5, 17 | $NaHCO_3$, 7.7 | EDTACu, 0.36 | $N_2$, 80 | $H_2O$, 25 | 50 | 140 | 4.0 | 4.0 |

| Exper. No. | Conv. % | 1-AAQCA % | AQCA % | DAAQCA % | Unkn. % | 1-AAQCA Yield (%)$^a$ |
|---|---|---|---|---|---|---|
| 1 | 99 | 85 | 3.5 | 8.0 | 2.5 | 85 |
| 2 | 100 | 82 | 1.3 | 7.0 | 10.0 | 80 |
| 3 | 97 | 87 | 1.8 | 2.0 | 5.0 | 83 |
| 4 | 98 | 83 | 1.2 | 6.0 | 5.0 | 78 |
| 5 | 99 | 80 | 3.9 | 9.0 | 3.0 | 75 |
| 6 | 98 | 81 | 4.1 | 4.0 | 4.0 | 76 |
| 7 | 95 | 91 | 1.1 | 6.0 | 3.0 | 90 |
| 8 | 99 | 74 | 1.6 | 3.0 | 4.5 | $50^c$ |
| 9 | — | 0.0 | 0.0 | 0.0 | 0.0 | 0 |
| 10 | 44 | 49.5 | 0.0 | 0.0 | 4.0 | 46 |
| 11 | 49 | 7.8 | 23.0 | 23.0 | 7.5 | 8 |
| 12 | 40 | 3.6 | 2.2 | 0.0 | 11.5 | 3 |
| 13 | 40 | 29.5 | 1.9 | 0.0 | 5.0 | 31 |
| 14 | 99 | 78.6 | 4.3 | 4.3 | 5.5 | 70 |

TABLE III-continued

Synthesis of 1-Aminoanthraquinonecarboxylic Acids (1-AAQCA) from 1-Chloroanthraquinonecarboxylic Acids (1-CAQCA).

| | | | | | | |
|---|---|---|---|---|---|---|
| 15 | 55 | 41.9 | 4.0 | 1.5 | 4.5 | 43 |
| 16 | 100 | 74.6 | 6.0 | 4.9 | 6.0 | 77 |
| 17 | 97 | 6.3 | 0.7 | 29.5 | 6.0 | 3 |
| 18 | 99 | 74.3 | 6.7 | 0.0 | 8.0 | 76 |
| 19 | 99 | 70.7 | 5.9 | 7.0 | 6.0 | 73 |
| 20 | 31 | 26.0 | 2.1 | 0.0 | 6.0 | 24 |
| 21 | 99 | 76.2 | 8.4 | 0.0 | 11.0 | 68 |
| 22 | 97 | 69.3 | 9.6 | 0.0 | 9.0 | 67 |
| 23 | 95 | 64.0 | 11.3 | 0.0 | 10.0 | 57 |
| 24 | 98 | 66.7 | 13.7 | 1.7 | 8.0 | 60 |
| 25 | 96 | 81.5 | 6.9 | 7.4 | 4.0 | 73 |
| 26 | 92 | 75.6 | 5.1 | 1.7 | 5.0 | 69 |
| 27 | 98 | 77.9 | 7.6 | 2.0 | 6.0 | 70 |
| 28 | 97 | 75.5 | 7.4 | 2.0 | 6.0 | 76 |
| 29 | 95 | 73.1 | 9.3 | 2.1 | 7.0 | 65 |
| 30 | 99 | 86.0 | 6.5 | 4.5 | 5.0 | 81 |
| 31 | 99 | 86.1 | 6.4 | 1.3 | 4.0 | 77 |

[a]Yield was determined on the basis of response factor analysis via HPLC.
[b]48% aqueous ammonia was used in this reaction.
[c]Product was lost due to incomplete acidification.
[d]o-Dichlorobenzene.
[e]Grams of anhydrous ammonia was used.
[f]Hydrogen peroxide (0.2 g) was also added.
[g]Sodium sulfite (0.3 g) was also added.

EXAMPLE 5

Decarboxylation of 1-aminoanthraquinone carboxylic acid (1-AAQCA).

Process conditions and product yields are shown in Table IV. The decarboxylation of 1-AAQCA was carried out in several solvents, e.g., N-methylpyrrolidone, pyridine, quinoline and acetic acid. The best results were obtained in pyridine. When decarboxylation of 1-AAQCA was carried out with 5 mol % of copper powder in pyridine at 260° C. for 2.5 hours, complete conversion was observed. Distillation of the crude product afforded 1-aminoanthraquinone (1-AAQ) in 64% yield. We were unable to decarboxylate 1-AAQCA in pyridine alone, without a copper catalyst. Decarboxylation of 1-AAQCA in quinoline using 5 mol % of copper powder gave 1-AAQ in 65% yield.

TABLE IV

Synthesis of 1-Aminoanthraquinone (1-AAQ) from 1-Aminoanthraquinonecarboxylic Acids (1-AAQCA)

| Exper. No. | 1-AAQCA (g. mmol) | Catalyst (g. mmol) | Solvent (mL) | Temp[a] (°C.) | Temp (h) | Total wt. (g) | Conv. (%) | 1-AAQ (mmol) | 1-AAQ Yield (%)[d] |
|---|---|---|---|---|---|---|---|---|---|
| 1 | 5.0, 18.7 | CuO (0.15, 1.9) | Quin. (10) | 230 | 56.5 | 3.1[b] | 100 | 8.2 | 44 |
| 2 | 5.0, 18.7 | Cu (0.25, 3.9) | Quin. (50) | 260 | 2.0 | 2.5 | 100 | 7.3 | 65 |
| 3 | 10.0, 37.5 | Cu (0.5, 7.8) | Quin. (50) | 260 | 2.5 | 7.8 | 100 | 19.9 | 57 |
| 4 | 5.0, 18.7 | Cu (0.25, 3.9) | Pyri. (50) | 260 | 1.0 | 4.8[c] | 40 | 7.1 | 38 |
| 5 | 4.8, 18.0 | Cu (0.25, 3.9) | Pyri. (75) | 260 | 2.5 | 3.8[c] | 100 | 11.4 | 64 |
| 6 | 5.0, 18.7 | No catalyst | Pyri. (75) | 260 | 2.0 | — | 0.0 | 0.0 | 0.0 |
| 7 | 5.3, 19.8 | CuSO$_4$ (0.52, 2.0) | Pyri. (75) | 250 | 5.5 | 4.6 | 99 | 11.8 | 59 |
| 8 | 5.3, 16.1[e] | Cu (0.16, 2.5 | Pyri. (75) | 250 | 2.0 | 4.6[c] | 100 | 12.4 | 77 |
| 9 | 5.3, 16.1[e] | CuO (0.2, 2.5) | Pyri. (75) | 250 | 2.0 | 4.5[c] | 100 | 11.5 | 71 |
| 10 | 5.3, 17.4[f] | Cu (0.25, 3.9) | Pyri. (75) | 250 | 2.5 | 4.5[c] | 100 | 12.4 | 71 |
| 11 | 5.0, 16.4[f] | CuO (0.25, 3.1) | Quin. (20) | 238 | 6.0 | 3.8 | 100 | 10.2 | 62 |

[a]Decarboxylations were carried out in a sealed autoclave under N$_2$ pressure. Quinoline runs were carried out at atmospheric pressure.
[b]In quinoline runs the product is isolated by drowning the reaction mixture in dil. HCl followed by filtration of the product.
[c]In pyridine runs, the product was isolated after removing the pyridine in-vacuo.
[d]Yield was determined on the basis of response factor analysis via HPLC.
[e]81% pure 1-AAQCA was used.
[f]88% pure 1-AAQCA was used.

What is claimed is:

1. A process for producing a compound of the formula

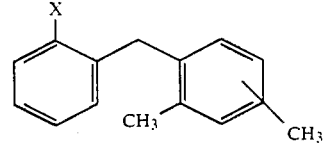

comprising reacting a benzyl compound having the structural formula:

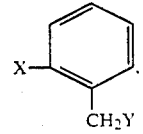

wherein X and Y may be the same or different and are selected from the group consisting of halogen, hydroxy, alkoxy, thioalkyl, nitro, and sulfonyl, with xylene in the presence of a solid acid catalyst consisting of a member of the group consisting of alumina, silica-alumina, aluminophosphates, aluminosilicates, and silicalites.

2. The process of claim 1 wherein the reaction is carried out in the liquid phase at a temperature ranging from about 80° C. to about 160° C.

3. The process of claim 2 wherein the temperature is within the range of 100° C. to 150° C.

4. The process of claim 1 wherein X and Y are both halogen.

5. The process of claim 4 wherein said halogen is chlorine.

6. The process of claim 1 wherein said xylene is meta-xylene.

7. The process of claim 1 wherein said xylene is para-xylene.

8. The process of claims 6 or 7 wherein X and Y are both halogen.

9. The process of claim 8 wherein said halogen is chlorine.

10. The process of claim 1 wherein said catalyst is silica-alumina.

11. A process for preparing 1-aminoanthraquinones from a 2-substituted benzyl compound having the structural formula:

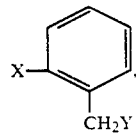

wherein X and Y may be the same or different and are selected from the group consisting of halogen, hydroxy, alkoxy, nitro and sulfonyl, which comprises the steps of (i) reacting said 2-substituted benzyl compound with xylene in the presence of a solid acid catalyst consisting of a member of the group consisting of alumina, silica-alumina, aluminophosphates, aluminosilicates, and silicalites for a period of time sufficient to obtain a 2-substituted dimethyldiphenylmethane, (ii) oxidizing said 2-substituted dimethyldiphenylmethane for a period of time sufficient to obtain a 2-substituted benzophenonedicarboxylic acid; (iii) contacting said benzophenonedicarboxylic acid with an acid for a period of time sufficient to obtain a 1-substituted anthraquinonecarboxylic acid; and (iv) contacting said anthraquinonecarboxylic acid with ammonia or an amine of the formula RNH$_2$ wherein R is alkyl, cycloalkyl, or aryl for a period of time sufficient to obtain a 1-aminoanthraquinone-carboxylic acid.

12. The process of claim 11 further comprising (v) decarboxylating said 1-aminoanthraquinonecarboxylic acid to obtain 1-aminoanthraquinone.

13. The process of claim 12 wherein steps (iv) and (v) are carried out in the presence of a copper catalyst.

14. The process of claim 11 wherein step (iv) is carried out in the absence of a catalyst.

15. The process of claim 11 wherein said oxidizing in step (ii) is achieved by air oxidation of said 2-substituted dimethyldiphenylmethane.

16. The process of claim 15 wherein said air oxidation in done in the presence of a cobalt-manganese-bromide catalyst.

17. The process of claim 15 wherein said oxidation of 2-substituted dimethyldiphenylmethane produces a product mixture comprising 2-chloro-2',5'-benzophenonedicarboxylic acid and 1-chloroanthraquinone-6/7-carboxylic acid.

18. The process of claim 11 wherein said benzophenone dicarboxylic acid is contacted in step (iii) with a strong acid catalyst.

19. The method of claim 18 wherein said strong acid catalyst is selected from the group consisting of oleum, sulfuric acid, phosphoric acid, HF, or HF/BF$_3$.

20. The process of claim 19 wherein said strong acid catalyst is oleum in concentrated sulfuric acid.

21. The process of claim 11 wherein said xylene is meta-xylene.

22. The process of claim 11 wherein said xylene is para-xylene.

23. The process of claim 11 wherein each X and Y are both halogen.

24. The process of claim 23 wherein said halogen is chlorine.

25. The process of claim 11 wherein said catalyst is silica-alumina.

26. The process of claim 11, wherein said decarboxylation of 1-aminoanthraquinonecarboxylic acid is conducted in a nitrogen-containing aromatic heterocyclic solvent.

27. The process of claim 26 wherein said solvent is selected from the group consisting of quinoline, pyridine, lutidine and collidine.

28. The process of claim 27 wherein said solvent is quinoline or pyridine.

29. The process of claim 11, wherein the decarboxylation is carried out at a temperature ranging from about 220° C. to about 280° C.

30. The process of claim 29 wherein the decarboxylation is carried out at a temperature ranging from about 250°–260° C.

* * * * *